United States Patent
Matz

(10) Patent No.: US 7,357,308 B2
(45) Date of Patent: Apr. 15, 2008

(54) SYSTEM AND METHOD OF AUTOMATICALLY DISPLAYING PATIENT INFORMATION

(75) Inventor: William Randolph Matz, Atlanta, GA (US)

(73) Assignee: AT&T BLS Intellectual Property, Inc., Wilmington, DE (US)

(*) Notice: Subject to any disclaimer, the term of this patent is extended or adjusted under 35 U.S.C. 154(b) by 470 days.

(21) Appl. No.: 10/611,250

(22) Filed: Jun. 30, 2003

(65) Prior Publication Data

US 2004/0262377 A1    Dec. 30, 2004

(51) Int. Cl.
*G06K 5/00* (2006.01)
(52) U.S. Cl. .................. 235/380; 235/375
(58) Field of Classification Search ........... 235/375, 235/380, 385, 462.01; 705/2–5
See application file for complete search history.

(56) References Cited

U.S. PATENT DOCUMENTS

| | | | |
|---|---|---|---|
| 3,597,742 A * | 8/1971 | Philipps et al. | 235/375 |
| 4,835,372 A * | 5/1989 | Gombrich et al. | 235/375 |
| 4,857,716 A * | 8/1989 | Gombrich et al. | 235/375 |
| 5,732,401 A * | 3/1998 | Conway | 705/29 |
| 5,737,539 A * | 4/1998 | Edelson et al. | 705/3 |
| 5,822,544 A * | 10/1998 | Chaco et al. | 705/2 |
| 5,867,821 A * | 2/1999 | Ballantyne et al. | 705/2 |
| 6,381,576 B1 * | 4/2002 | Gilbert | 705/2 |
| 2004/0172284 A1 * | 9/2004 | Sullivan et al. | 705/2 |

* cited by examiner

*Primary Examiner*—Michael G. Lee
*Assistant Examiner*—Kumiko C. Koyama
(74) *Attorney, Agent, or Firm*—Scott P. Zimmerman, PLLC; Geoff Sutcliffe

(57) ABSTRACT

Systems and methods of automatically or semi-automatically loading patient chart information onto a patient room computer system. The systems and methods involve using the patient room computer system to obtain patient identifying information, then requesting the patient chart from a primary computer system. Upon receiving the patient chart from the primary computer system, the invention relates to displaying the patient chart on the patient room computer system. Obtaining the patient information may occur in several ways. For instance, since a patient is typically associated with a specific room within the healthcare facility, the act of obtaining patient information may involve determining the room identification for the patient and using the room identification, requesting the patient chart associated with the room. In an embodiment, the room identification information is transmitted to the patient room computer system automatically upon entering the room, e.g., by using cellular telephone technology. In another embodiment, the patient room computer system has bar-code reading capabilities and thus reads a bar-code, either as part of the room providing room information as part of the patient providing patient identification information independent of room information.

17 Claims, 9 Drawing Sheets

SYSTEM AND METHOD OF AUTOMATICALLY DISPLAYING PATIENT INFORMATION

FIELD OF THE INVENTION

The present invention relates to the medical industry and, in particular, to methods of managing patient records. More particularly, the present invention relates to the manner in which patient records are stored and used, including the contemporaneously viewing and updating of patient charts during actual patient care activities.

BACKGROUND OF THE INVENTION

During a typical office visit to a physician or other medical professional (hereinafter "healthcare professional"), whether in an office or a hospital, a separate patient chart is created for each new patient. This chart lists all the relevant information related to that patient such as medical history and specific medical needs. The chart typically includes other pertinent information such as the patient's personal identification information such as their name, address, billing information, emergency contact, etc. Indeed, the chart is the primary document maintained in most medical arenas. During subsequent visits this chart is pulled and handed to the healthcare professional for contemporaneously taking notes and making a record of discussions and advice given to the patient. The chart also typically contains information related to prescriptions written by the healthcare professional during particular visits. Since the chart is in paper form, it is handed back and forth between assistants and secretaries as part of the patient care process. Furthermore, such a chart may be handed to or passed through the accounting department for proper insurance and patient billing.

Significant drawbacks related to these paper charts are encountered on a daily basis in numerous healthcare facilities. For example, paper charts are often damaged, lost or misplaced. In particular, in a hospital environment, the patient charts are easily confused and therefore misplaced. In such an environment, the primary doctor often does not know the patient personally as it may be the first time that particular doctor has seen the patient such that the doctor may be unaware that the patient chart is incorrect in some instances. Adding to this, sometimes the patient is unable to communicate with the doctor such that the doctor must rely on the chart handed her or located in the room with the patient. Obviously, a lost or misplaced chart creates a very difficult situation because the re-creation of such information is nearly impossible. Other times the situation may be time critical such that re-creation of the information would simply take too long. Thus, a lost chart is not only time consuming but potentially dangerous as well.

Another significant problem associated with the paper charts relates to the legibility of the handwritten notes. Indeed, failure to accurately read a medical chart may result in the improper prescription of certain drugs, which can be very dangerous. Furthermore, although not often recognized as a problem, the paper charts may in fact aid in the transmission of diseases as the charts are reused and passed from room to room without disinfection. The inadvertent transmission of diseases is, of course, a dangerous situation.

These problems all directly impact the safety and satisfaction of patients and the care that they are given and it is with respect to these and other considerations that the present invention has been made.

SUMMARY OF THE INVENTION

The present invention relates to a computerized patient chart system that involves a patient room computer system for the contemporaneous display and maintenance of patient medical information, i.e., edits and additions to the patient chart. Since the patient room computer is available during the visit, the healthcare professional can enter information on the computer system to reduce errors associated with legibility. Also, since the chart is kept on the computer system, paper charts are not used and therefore do not get lost as the system can be backed up and saved in many different, and protected ways. Also, since paper charts are not being handled, the chance of disease transmission is reduced. Further, since the system is computerized, different program modules may be incorporated to double check the suitability of information entered, e.g., the accuracy/appropriateness of prescriptions for a given patient, etc.

In accordance with other aspects of the present invention, the patient room computer system is connected, via a network, to a primary computer system. The primary computer system, in an embodiment, relates to another computer system located at the nurse's station or some other location. During a particular patient visit, the primary computer system may simultaneously display the patient chart (along with contemporaneous updates) to improve the service provided to the patient. Further, other computer systems, such as a doctor's remote computer system, may access the information.

In accordance with certain aspects, the present invention relates to systems and methods of automatically or semi-automatically loading patient chart information onto a patient room computer system. The systems and methods involve using the patient room computer system to obtain patient identifying information, then requesting the patient chart from a primary computer system. Upon receiving the patient chart from the primary computer system, the invention relates to displaying the patient chart on the patient room computer system.

Obtaining the patient information may occur in several ways. For instance, since a patient is typically associated with a specific room within the healthcare facility, the act of obtaining patient information may involve determining the room identification for the patient and using the room identification, requesting the patient chart associated with the room. In an embodiment, the room identification information is transmitted to the patient room computer system automatically upon entering the room, e.g., by using cellular telephone technology. In another embodiment, the patient room computer system has bar-code reading capabilities and thus reads a bar-code, either as part of the room providing room information as part of the patient providing patient identification information independent of room information.

The invention may be implemented as a computer process, a computing system or as an article of manufacture, such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

A more complete appreciation of the present invention and its improvements can be obtained by reference to the accompanying drawings, which are briefly summarized

DETAILED DESCRIPTION

Figure 1:
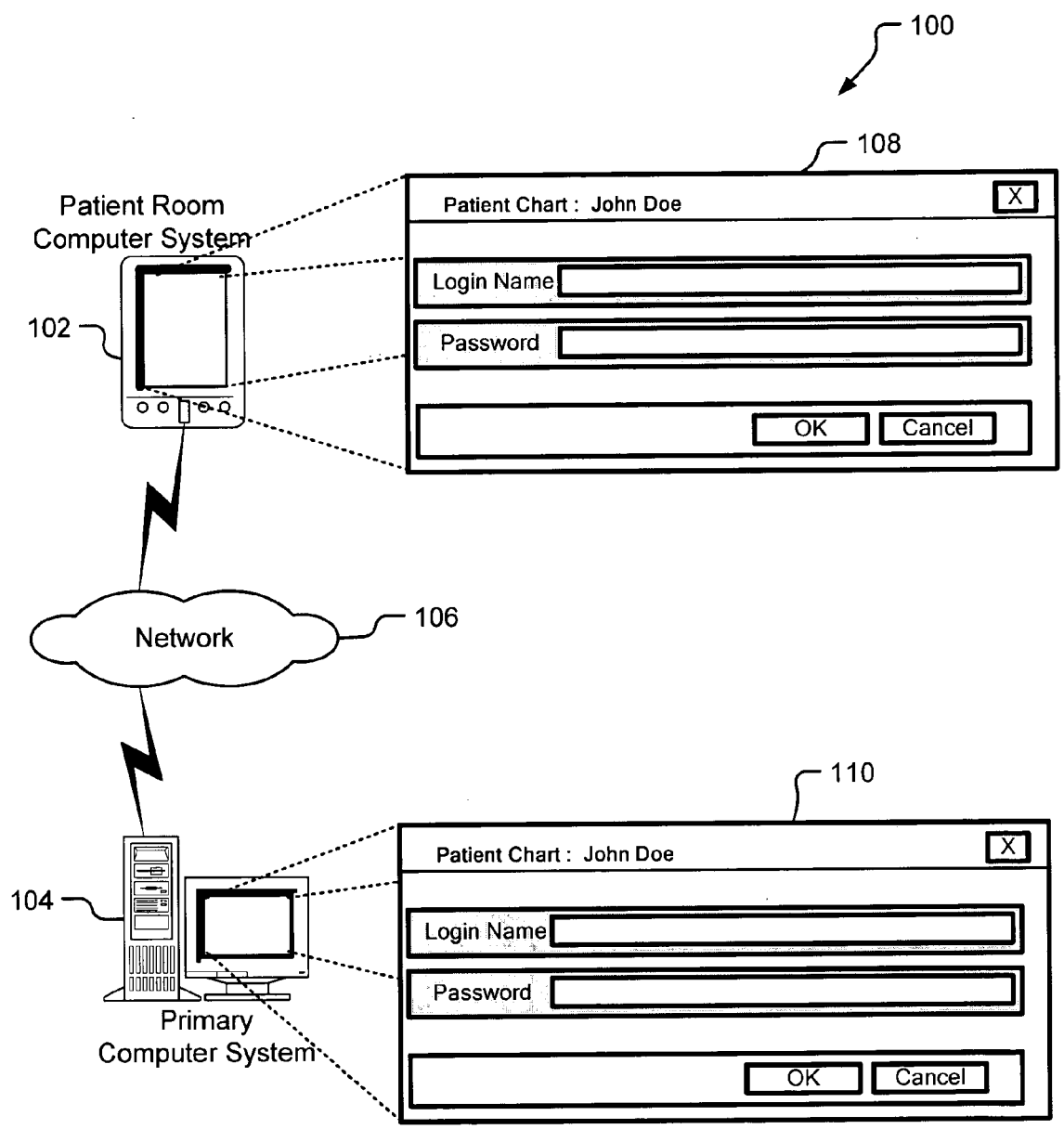
FIG. 1 is a block diagram illustrating the environment for the present invention including a networked system for entering and managing patient information.

The present invention relates to a computerized network in a healthcare environment. A distributed environment 100 incorporating aspects of the present invention is shown in FIG. 1. The environment 100 relates to a distributed network having at least one patient room computer system 102 that communicates with at least one primary computer system 104. The client computer system 102 and the server computer system 104 communicate using a communication protocol over the distributed network 106. In one embodiment, the communication network 106 is an intranet. In other embodiments, the network 106 utilizes the Internet. The patient room computer system 102 is used to display an electronic or computerized version of a patient chart having patient information, and to edit the same, thereby eliminating the need for paper-based patient charts.

The patient room computer system 102 receives and displays data entered by the doctor or other healthcare professional providing patient care to the patient. The system 102 allows the healthcare professional to enter the information contemporaneously with the patient visit, i.e., during or shortly after the patient visits the healthcare professional. Although the healthcare professional typically enters such information, as may be understood, many different individuals may utilize this system to record information related to a particular patient and/or visit, including nurses, administrators, staff employees, etc.

The patient room computer system 102 displays the patient chart for a visiting patient. In an embodiment, the healthcare professional can access the information by connecting to the network 106 and requesting the chart for a particular patient. Access to the chart may require a login name and password to be entered in order to access the patient information. An exemplary login screen for a particular patient, e.g., John Doe, is shown as screen shot 108 in FIG. 1. This login provides security for the patient information as only those persons knowing the login name and password can access the information. Also, as shown in FIG. 1, the patient chart may be accessed from both the patient room computer system 102 and the primary computer system 104. When accessing the patient chart from the system 104, a similar login screen 110 is provided for security purposes.

In another embodiment, such as when the patient room computer 102 is a mobile device, the relevant patient information may be automatically displayed upon entering the patient's room. Alternatively, the login screen may be automatically displayed. However, when the device is a mobile device, some security may be relaxed since it is assumed the holder of the device is authorized to view patient information. Of course, many other known security methods and procedures may be implemented to protect the patient's privacy.

The automatic display of patient chart information upon entering the patient's room may be achieved in different ways. For instance, in one embodiment the patient room computer system 102 receives a wireless communication from a transmitting/receiving devices (not shown) located in the patient's room upon entering that room. Consequently, the patient room computer system recognizes that it has entered a new room upon receiving a new signal. Using this room-identification information, the patient room computer system 102 communicates, using similar wireless communication technology with the primary computer system 104. These communications may enable the primary computer system to understand the location of the patient room computer system and hence, which information should be downloaded and displayed on the patient room computer system 102.

Alternatively, the patient room computer system may have bar-code reading capabilities. In such a case, the room may have an associated bar-code, such as on door or in some other area of the room. Thus, the healthcare professional need only scan the bar code to identify the room location, transmit the same to the primary computer system 104 to thus receive the relevant patient information in such a semi-automatic manner.

In yet another embodiment, the patient may have an associated bar-code, e.g., printed on a bracelet, and the healthcare professional need only scan this information. In this embodiment, the room location is not relevant, as the primary computer system can download the proper information for the patient independent of where the patient room computer system is located.

In a particular embodiment of the present invention, when both computer systems 102 and 104 have correctly accessed a patient's chart, the displays are linked and information provided on one system 102 or 104, is substantially simultaneously shown on the other system 104 or 102 respectively. Providing the simultaneous display on the two systems 102 and 104 provides a monitoring capability for the healthcare facility. In yet another embodiment, some of the monitoring functionality can be handled by the computer system, e.g. 102 or 104, itself. More details on simultaneous display and the automated monitoring functions can be found in U.S. patent application Ser. No. 10/610,777, entitled SYSTEM AND METHOD FOR MONITORING PATIENT HEALTHCARE INFORMATION DURING A VISIT, incorporated herein by reference for all that it discloses and teaches, filed concurrently herewith, and assigned to the Assignee of the present application.

Figure 2:
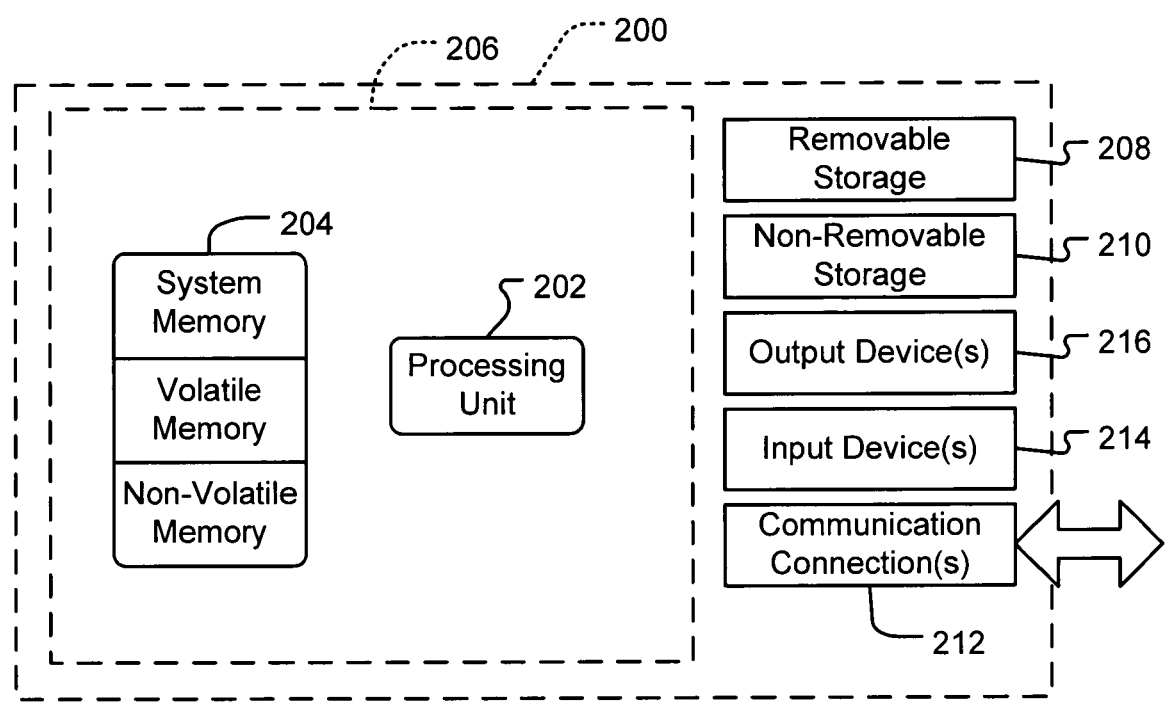
FIG. 2 illustrates a computer system that may be utilized in an embodiment of the present invention.

The computer systems, such as 102 and 104 may be represented by the computer system 200 shown in FIG. 2. The system 200 has at least one processor 202 and a memory 204. In its most basic configuration, computing system 200 is illustrated in FIG. 2 by dashed line 206 encompassing the processor 202 and the memory 204. Additionally, system 200 may also include additional storage (removable and/or non-removable) including, but not limited to, magnetic or optical disks or tape. Such additional storage is illustrated in FIG. 2 by removable storage 208 and non-removable storage 210. Computer storage media, such as memory 204, removable storage 208 or non-removable storage 210 includes volatile and nonvolatile, removable and non-removable media implemented in any method or technology for storage of information such as computer readable instructions, data structures, program modules or other data. Memory 204, removable storage 208 and non-removable storage 210 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by system 200. Any such computer storage media may be part of system 200. Depending on the configuration and type of computing device, memory 204 may be volatile, non-volatile or some combination of the two.

System 200 may also contain communications connection(s) 212 that allow the device to communicate with other devices. Additionally, system 200 may have input device(s) 214 such as keyboard, mouse, pen, voice input device, touch input device, etc. Output device(s) 216 such as a display, speakers, printer, etc. may also be included. All these devices are well known in the art and need not be discussed at length here.

Computer system 200 typically includes at least some form of computer readable media. Computer readable media can be any available media that can be accessed by system 200. By way of example, and not limitation, computer readable media may comprise computer storage media and communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Figure 3:
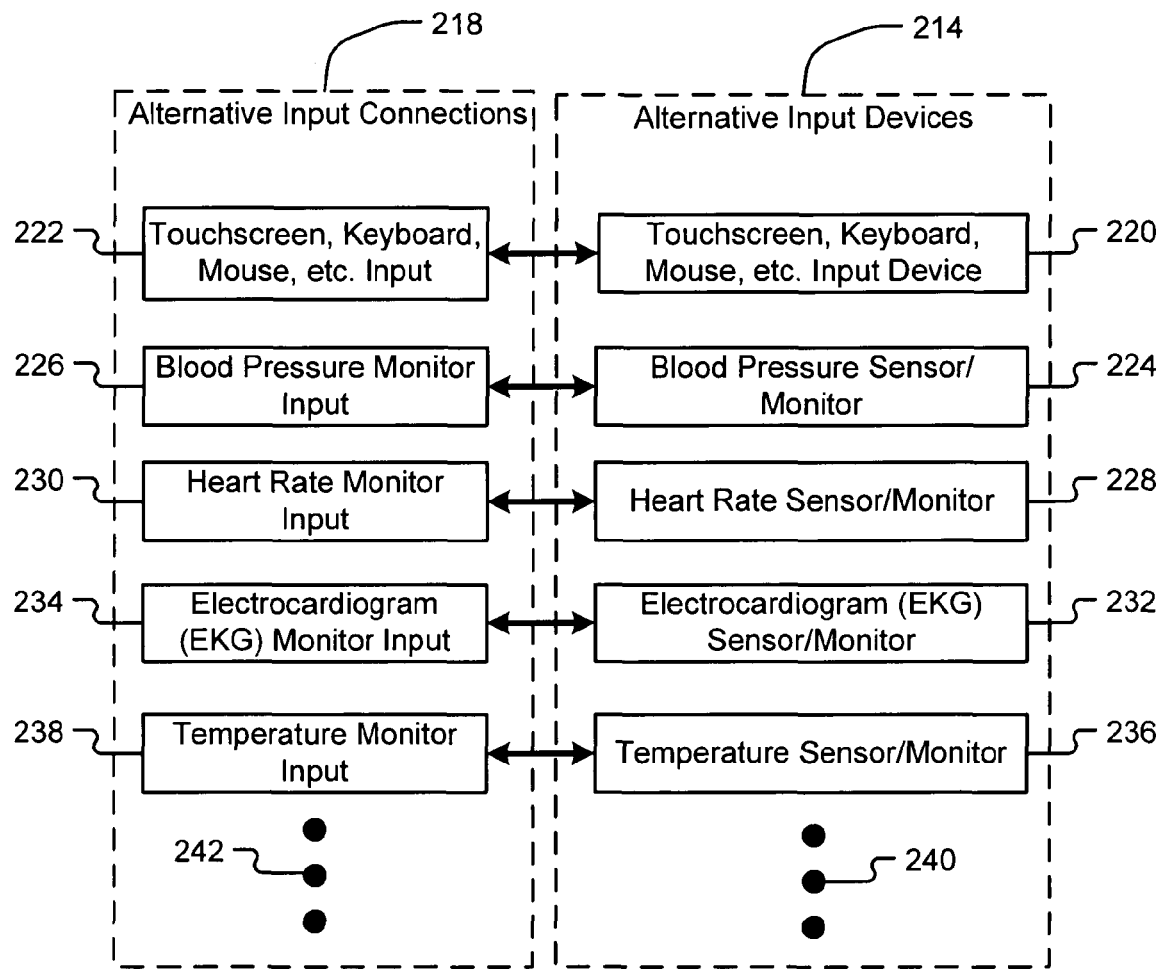
FIG. 3 illustrates a more detailed view of a particular computer as shown in FIG. 2 including automatic entry and remote entry capabilities and a particular embodiment.

As stated, the input devices 214 may include many different types of input devices. Some exemplary devices 214 are represented in FIG. 3. FIG. 3 also illustrates alternative input device connections 218. Although not shown in FIG. 2, the input connections 218 relate to the connection elements associated with the computer 200 and more particularly 206 to allow external input devices to communicate with the computer 206. For instance, the system 206 may receive input from more traditional devices 220 such as keyboard, mouse, pen, handwriting recognition, alphanumeric, voice input device, touch input device, etc. In order to receive input information from such devices, input connections 222 are used. The input connections 222 relate to the computer connections, whether serial, parallel, USB, AT, PS/2, etc. for receiving information from one of the devices 220.

In the embodiment shown in FIG. 3, other input devices are also used to provide input information to computer 206. For instance, a blood pressure sensor/monitor 224 may be connected to a blood pressure monitor input connection 226 for relatively automatically providing blood pressure information to the computer system 206. Similarly, a heart rate sensor/monitor 228 may be connected to a heart rate monitor input connection 230 for relatively automatically providing heart rate information to the computer system 206. Additionally, an electrocardiogram (EKG) sensor/monitor 232 may be connected to an electrocardiogram (EKG) monitor input connection 234 and a temperature sensor monitor 236 may be connected to a temperature monitor input connection 238 for relatively automatically providing EKG information and temperature information to the computer system 206, respectively. Furthermore, as may be understood, other items may also be used as indicated by ellipses 240 and 242.

Figure 4:
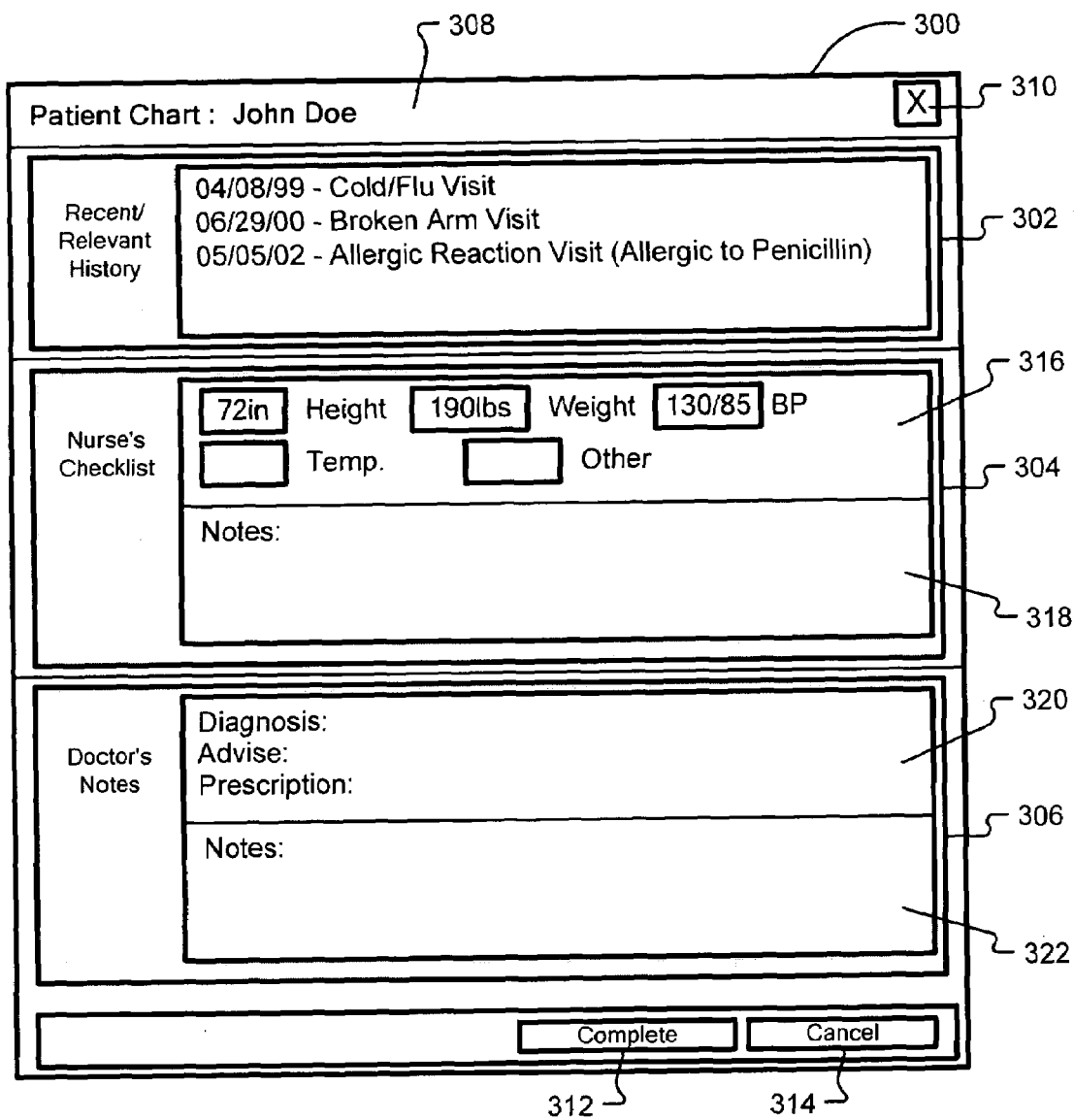
FIG. 4 illustrates a screen shot showing an exemplary graphical user interface for displaying and editing an electronic patient chart in accordance with an embodiment of the present invention.

In operation, during a visit, the healthcare professional retrieves a patient's chart on the patient room computer system, such as patient room computer system 102 shown in FIG. 1. A screen shot of an exemplary patient chart 300 is shown in FIG. 4. In this embodiment, the chart 300 is divided into at least three areas: a history area 302, a present-day checklist area 304, and a present diagnosis section 306. The chart also has a title bar 308 describing the patient and having a user-interface control 310 that allows the user to close the chart 300 when selected. The chart may further include user interface controls 312 and 314 that allow the user to update the chart, e.g., save the changes into memory using the "complete" control 312 or cancel and not save the changes using the "cancel" control 314.

In the history area 302, as shown in FIG. 4, many different historical items or information may be displayed. For instance a summary of recent visits may be displayed (as shown in FIG. 4). Alternatively, drug allergies may be shown, number of visits per year, recent types of prescribed medication, or almost any other type of historical data may be displayed. The area 302 may also include user-interface controls (not shown) to scroll through historical items or to select certain types of items to display. In an embodiment, the historical area may not be edited such that no accidental changes can be made.

The present-day checklist area 304, titled "Nurse's Checklist" includes two portions, a checklist portion 316 and a notes section 318. The checklist portion 316 provides text boxes for entering information related to the patient on the day of the visit. That is, when visiting a doctor or another health professional, a nurse typically gathers information about the patient, such as height, weight, blood pressure (BP), temperature and/or potentially other information. The area 304 provides a convenient means for entering the information and a checklist for reminding the nurse of the various items to be tested and/or information to be gathered. It is foreseeable that this area would be customizable to a particular practice depending on preferences of a particular healthcare professional. For instance, a podiatrist would care about different information than a general practice physician and thus the items in area 316 may be different for different healthcare professionals.

In addition to checklist portion 316, the nurse can enter notes to the healthcare professional by editing the notes section 318. That is, during a typical visit, the nurse visits with the patient first, gathering information in area 316 and to find out the purpose of the visit. The nurse can quickly make a note of the purpose of the visit, e.g., "pain in stomach" or "high temperature", etc. Subsequently, the healthcare professional is able to quickly ascertain the issues by reading the notes section 318. Of course, any other relevant notes may be entered into section 318.

The third area of the chart 300 relates to the healthcare professional's area 306. In the example shown in FIG. 4, the area 306 is titled "Doctor's Notes" and is divided into two sections, diagnosis area 320 and notes area 322. The diagnosis area 320 is generally reserved for the healthcare professional's specific diagnosis and advice given to the patient, as well as any prescriptions written for the patient. This information may become part of the permanent chart for the patient. The healthcare professional also has a notes section 322 for taking notes regarding the visit. This information may or may not become part of the permanent chart for the patient.

Figure 5:
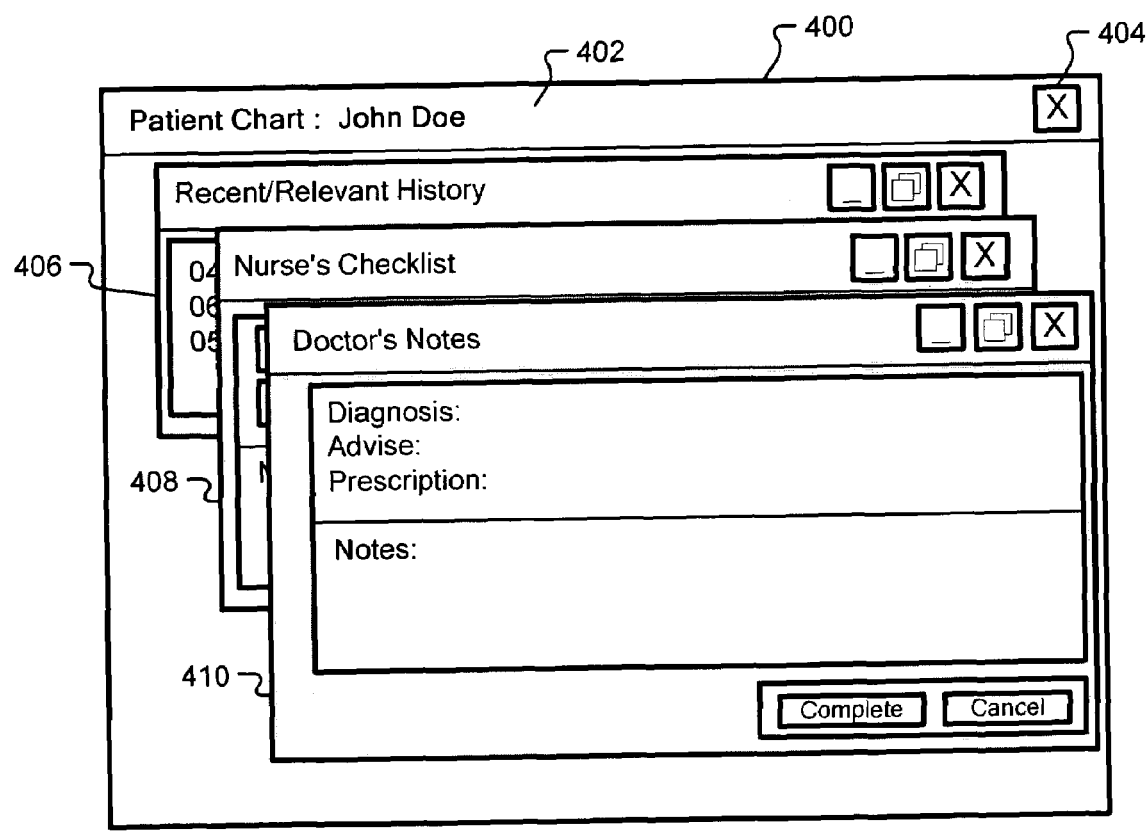
FIG. 5 illustrates a screen shot showing another exemplary graphical user interface for displaying and editing an electronic patient chart using a plurality of window controls in accordance with another embodiment of the present invention.

In another embodiment, different portions of a patient chart, such as chart 400, are presented as separate window elements, as shown in FIG. 5. Chart 400 incorporates a title bar 402 and a user-interface control element 404 to close the chart when selected. The chart 400 also has a plurality of sub-window elements, such as elements 406, 408 and 410. In this example the sub-window elements 406, 408 and 410 correspond to the different chart areas 302, 304 and 306 associated with chart 300 shown in FIG. 4. That is, element 406 is a relevant history window element that comprises similar information as relevant history area 302. Also, the window element 408 comprises similar information as the portion 304, including a checklist area and a notes area. Further, window element 410 is similar to the portion 306 shown and described in conjunction with FIG. 4.

As discussed above, FIGS. 4 and 5 illustrate examples of potential screens or graphical user interface elements that may be implemented in an embodiment of the present invention as part of the overall user interface. The purpose of these user interface elements is to display relevant information in a meaningful manner as well as provide a meaningful way to enter new, updated patient information so that it can be stored as part of the patient's medical chart and thus medical history. As may be appreciated, many other user interface elements, including but not limited to, pop up screens, menus, pop up menus, control elements, etc. may be designed to achieve this function. Consequently, FIGS. 4 and 5 are intended to be mere examples of electronic versions of patient chart information and the user interfaces for reading and editing the same.

The logical operations of the various embodiments of the present invention may be implemented (1) as a sequence of computer implemented steps running on one or more computing systems and/or (2) as interconnected machine logic modules within the computing systems. Accordingly, the logical operations making up embodiments of the present invention described herein are referred to variously as operations, acts, steps or modules as shown and described more fully below.

Figure 6:
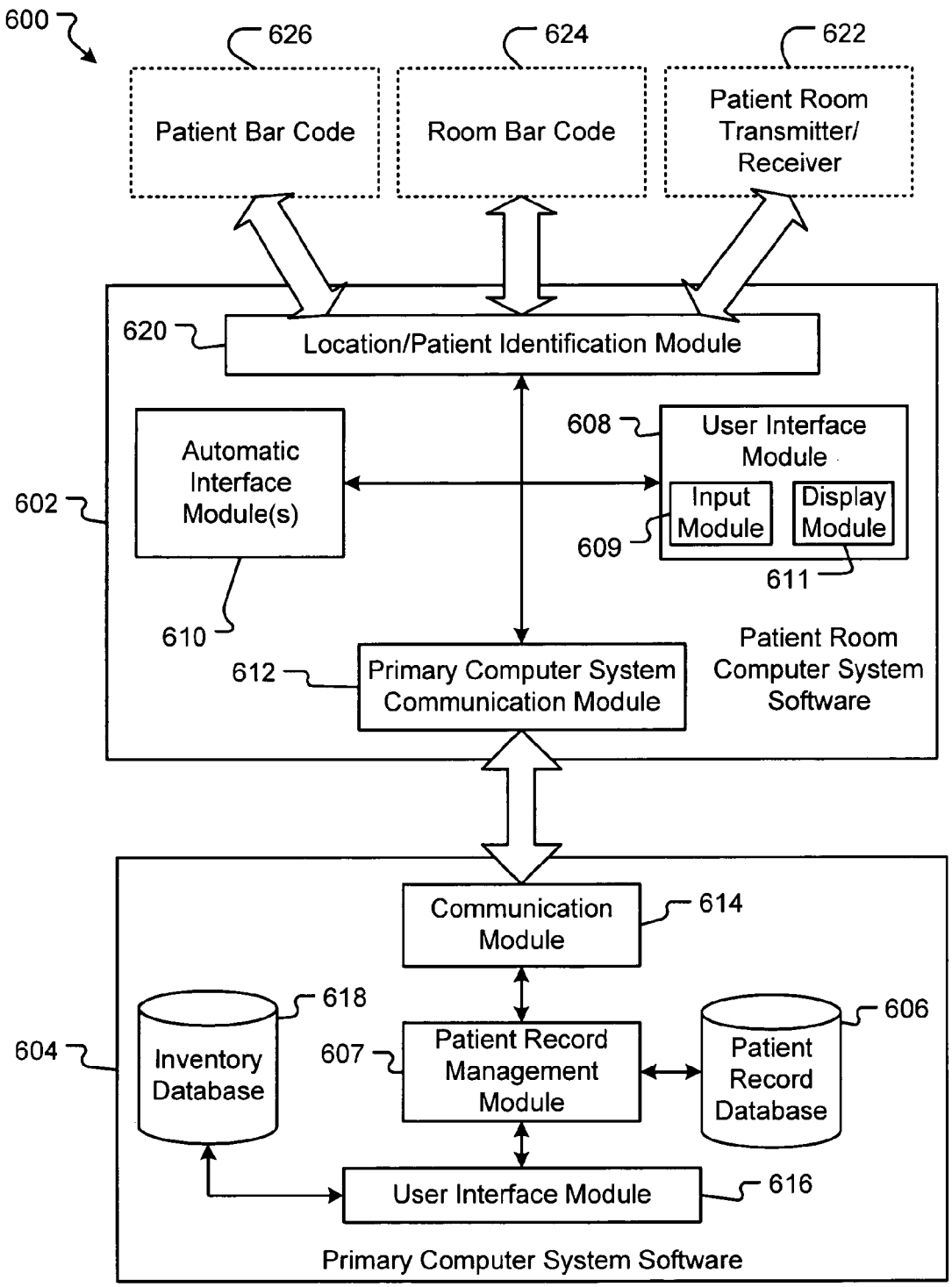
FIG. 6 illustrates software elements in an embodiment of the present invention.

FIG. 6 illustrates a software/hardware environment 600 incorporating aspects of the present invention. The environment 600 includes separate modules that perform functional operations in accordance with those aspects and wherein the modules are communicably connected as needed to perform certain functions as shown in FIG. 6. In general, the environment 600 comprises a patient room computer system or layer of software 602 and a primary computer system or layer of software 604, which, in one embodiment correspond respectively to the patient room computer system 102 and the primary computer system 104 shown in FIG. 1. The patient room computer system software 602 communicates with the primary computer system software 604 to automatically receive and later store patient charts. The primary computer software 604 accesses patient record databases, such as database 606, and, in other embodiments, other computer systems (not shown) to provide information to the patient room computer system software and to manage other patient needs. In the embodiment shown in FIG. 6, the management module 607 relates to the applications or other program elements used and accessed by a user to store, retrieve and otherwise manage the patient records stored in database 606.

The patient room computer system software layer 602 has a user interface module 608 to both provide information to a user, e.g., through a monitor, speakers or some other device and to receive data from a user, e.g., through a keyboard, touch screen, etc. The different types of input devices are described above in conjunction with FIGS. 2 and 3. The user interface module 608 provides the software functionality to receive data and display the same to the user. As may be appreciated, the user interface module 608 further includes both an input module 609 and a display module 611. The input module 609 may be used by a user of the patient room computer system to manually request a particular patient chart, to provide room or patient identification information in the request for the chart, to provide security related identification information and/or to simply enter updates to a particular patient's chart. The display module 611 is used primarily to display requested information such as a patient's chart.

The patient room computer system software layer 602 also has an automatic interface module or modules 610. These modules provide software support for the automatic data entry provided from some other system, such as the systems shown and described in conjunction with FIG. 3. For instance, in an embodiment, the blood pressure monitor may be connected to a computer system for reading, storing and displaying blood pressure. This monitor may be connected to the patient room computer system as discussed above in conjunction with FIG. 3 to transfer blood pressure information to the patient room computer system. When connected, the patient room computer software modules 610 provide the software communication support to allow the transfer of this information to the patient room computer system. Other modules 610 may be implemented to receive information from other sensors or monitors as shown in FIG. 3.

In one embodiment, the user interface module 608 receives data from the user and stores the information locally. In another embodiment, the information is transmitted to the software system 604 for storage on the primary computer software system. In order to transmit the information to the primary computer system software layer 604, the patient room computer system software layer 602 has a communication module 612. The communication module 612 communicates with communication module 614 located on the primary computer system software layer. In an embodiment, the communication modules 612 and 614 communicate over an intranet. In yet another embodiment, the modules 612 and 614 communicate over the Internet, or some other network configuration. In other embodiments the communication connection between 612 and 614 is wireless, while other embodiments employ non-wireless technology.

In addition to the communication module 614, the primary computer system software layer may incorporate many other software elements. For example, the layer 604 has a user interface module 616. The user interface module 616 is similar to the user interface module 608 in that it provides software support for receiving data from a user and displaying or providing information to the user. The actual module 616 may differ from module 608 in that the systems may have different user interface elements, e.g., a touch screen instead of a keyboard, or a mouse instead of a pen device, etc.

Another functional module that might exist on the primary computer system software layer 604 relates to an inventory database 618. The inventory database may house information related to various items kept in local inventory, e.g., medicine, samples, medical supplies, etc. A user may access such information though the user interface module 616.

With respect to the patient record database 606, it includes the various patient charts as well as other patient-related information. In operation, the healthcare professional accesses the patient chart, stored in the database 606, and upon making changes, stores the chart back to the record database 606.

In order to access the proper patient chart, the patient room computer system software 602 and its communication module 612 requests a patient chart from the primary computer system software 604. In order to access the proper patient chart, the patient room computer system software layer 602 must provide some identifying information to the primary computer system software layer 604. In some embodiments, the user of the patient room computer system may simply type or enter the requested information, such as the patient's name, in order to allow the primary computer system to access and send the proper information. Upon entering this information, the user may then manually request the patient chart by choosing a request control on the user interface which, in turn causes a communication module 612 to request the proper patient chart from the software layer 604.

In other embodiments, the patient room computer system software layer 602 utilizes a location/patient identification module to determine the identifying information needed to request the proper patient chart. In one embodiment, the identification module 620 communicates with a patient room transmitter/receiver module 622. In this embodiment, the patient room computer system substantially constantly transmits and receives information in a manner similar to a cellular telephone. The constant transmission and receipt of information allows the patient room computer system to receive information from the transmitter 622 which may be located in a patient room. This transmitter 622 provides information to the patient room computer system software 602, and in particular module 620, such as the room number information. The room number information may then be used in a subsequent request for patient chart information. In this embodiment, it is contemplated that the primary computer system can match the room number with the patient staying or waiting in that room such that the proper patient information can be provided to the patient room computer system software layer 602.

Also, it is contemplated that since the identification module may substantially constantly receive information from a patient room transmitter 622, the patient room computer system software layer may request a new patient chart when the room information changes, e.g., when the patient room computer system is moved from room to room. Thus, the display provided by the user interface module 608 may automatically be updated when the patient room computer system enters a new room with a different patient's information.

In other embodiments, the room identifying information may be entered by the user, either manually or automatically. Manually entering the room information involves the user manually typing or selecting the room information from a list. Automatically entering the room information involves other means of entering room information, such as by providing a bar-code reader as part of the patient room computer system identification module. In such a case the user may scan a room bar code 624 located on the door of the room or in some other convenient location. Bar codes and bar code readers are well known to those skilled in the art. Upon scanning the bar code, the patient room computer system can request the proper patient chart using the entered room information.

In yet another embodiment, the patient may have an associated bar code 626. The bar code may be printed on a bracelet or some other item connected to the patient's body or worn by the patient. In such a case the identification module is equipped with a bar code reader and the request for information includes the actual patient identification information. Thus, the room number is not necessary for obtaining the proper patient chart and providing the same to the patient room computer system software layer 602.

Figure 7:
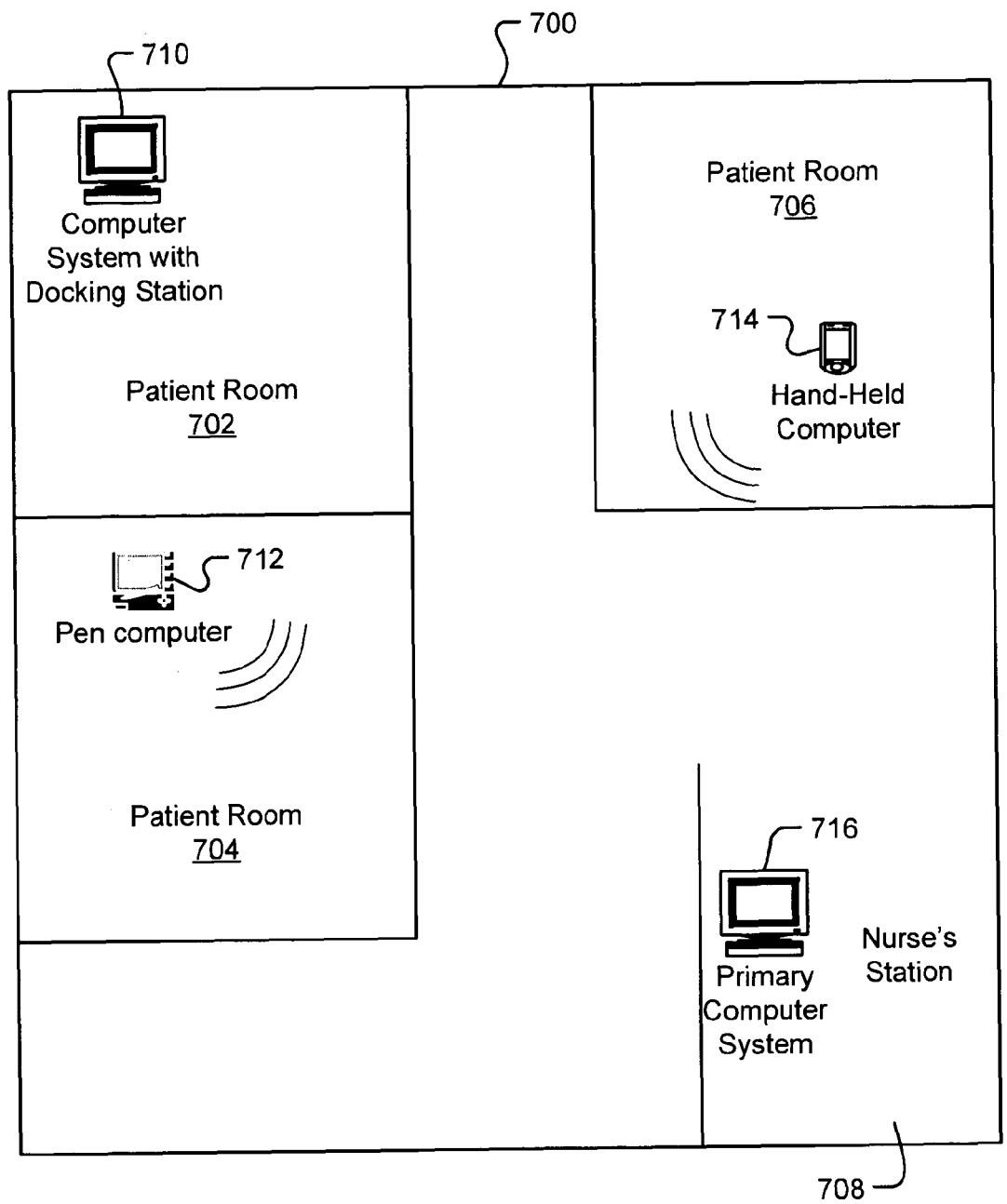
FIG. 7 illustrates an exemplary healthcare professional's office implementing concepts of the present invention, including different types of patient room computer systems.

An exemplary healthcare professional's office 700 utilizing aspects of the present invention is shown in FIG. 7. Although described as an office, is should be recognized that this may relate to a portion of a hospital, clinic or some other patient care facility. In particular, the office 700 includes three patient rooms 702, 704 and 706. The patient rooms are separate meeting rooms where the healthcare professional will meet with different patients. The office 700 also has a nurse's station 708. The station 708 may have many different elements, including filing cabinets, medicine cabinets, etc. The nurse's station 708, in an embodiment, has one or more nurses or other support staff present during patient visits.

In the exemplary environment shown in FIG. 7, located inside each of the patient rooms 702, 704 and 706 is a computer system. As shown in FIG. 7, the computer may be in the form of a workstation 710 (patient room 702), a pen computer 712 (patient room 712), or a hand-held computer system 714 (patient room 706). Each of the different computer systems 710, 712 and 714 communicate with a primary computer system 716. In the embodiment shown in FIG. 7, the primary computer system is located in the nurse's station 708. The different computers 710, 712 and 714 are shown in FIG. 7 to illustrate that many different types of computer systems may be used in accordance with the present invention. Indeed, many other types of computer systems that are not shown may also be used as patient room computer systems, as long as it communicates with the primary computer system to send and receive patient record or chart information.

As may be understood, the computer system 710 represents an example of a patient room computer system 102 shown in FIG. 1. As shown, the computer 710 is a workstation designed to remain within the patient room 702, i.e., it is not mobile. The workstation 710 may be used to enter information during a patient visit and to display a patient's chart to a user, among other things, as discussed above. In this embodiment, the workstation 710 is connected via wires to the primary computer system 716, i.e., it is hard-wired to the primary computer system 716. In another embodiment, the workstation 710 may be connected to an intermediate server computer system (not shown). In such an embodiment, the primary computer system 716 would also be connected to the server computer system (not shown) such that the workstation 710 and the primary computer system 716 communicate with each other.

Office 700 also demonstrates two other types of patient room computer systems 102, i.e., pen computer system 712 and hand-held computer system 714. The pen computer system 712 relates to a computer system that has different input functionality, such as a pen input instead of, or in addition to, a more traditional keyboard/mouse input system. The hand-held computer system 714 relates to a portable computer system that a healthcare professional may carry from room to room. The hand-held computer system may have a touch screen and/or other types of input/output functionality that is different from other patient room computer systems 710 and 712.

One difference between the systems 712 and 714 from the workstation 710, as shown in FIG. 7, is that the systems 712 and 714 are meant to illustrate the use of wireless computer systems that communicate with the primary computer system. As such, the pen computer system 712 and hand-held computer system 714 transmit information in a wireless manner to a receiver (not shown) which then communicates the information to the primary computer system 716. The receiver may be located in or on the primary computer system 716 or as part of another system, such as a server system (not shown). Repeaters may also be employed to aid in the sending and receiving of such information.

Importantly, in an embodiment, the primary computer system also has wireless capabilities to transmit information to the pen computer 712 and/or the hand-held computer system 714. As a result, the systems 712 and 714 receive important information related to a patient from the primary computer system when necessary. Furthermore, when using a mobile system, the device may be used from room to room, automatically receiving and displaying information related to the relevant patient, independent of which room the patient is located.

In an embodiment, the systems 710, 712 and 714 communicate with the primary computer system 716 via a local intranet system. However, in other embodiments, the systems 710, 712 and 714 may communicate with the primary computer system 716 via a wide area network, and in some cases the network is the Internet. As such, a health professional may visit a patient in another building, such as a hospital, or at their home, and the health professional may communicate with the primary computer system 716 to both transmit information and receive information.

Figure 8:
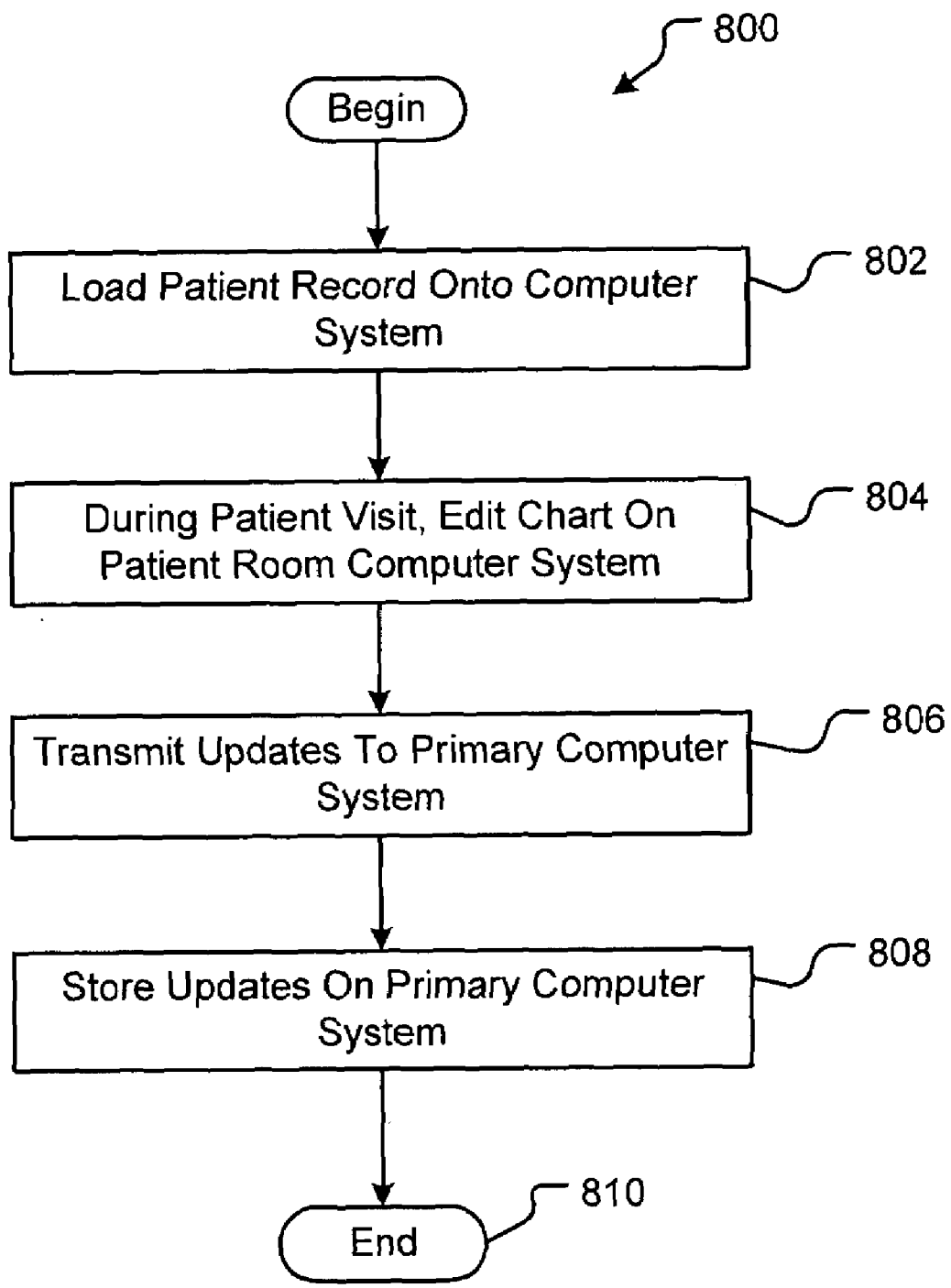
FIG. 8 illustrates a flowchart of functional operations related to entering information into a patient chart and storing the same on a primary computer system.

FIG. 8 illustrates a flowchart of functional operations related to entering information into a patient chart and displaying the same on a primary computer system. Initially, flow 800 begins with load operation 802. Load operation loads patient record information onto a patient room computer system, such as patient room computer system 102 shown and described in conjunction with FIG. 1 above. In an embodiment, before the patient record or chart can be loaded on the patient room computer system 102, the chart must be entered onto a primary computer system, such as system 104 shown and described above in conjunction with FIG. 1. Many known methods of entering data may be implemented when initially loading the information onto the primary computer system, e.g., typing the information or scanning the information may be exemplary data entry methods.

Once a patient's chart has been loaded on the primary computer system, load operation 802 loads the chart on the patient room computer system, such as system 102. In an embodiment, a healthcare professional uses the patient room computer system 102 to access the chart. Such a process may involve the transmission of a request to the primary computer system, including the type of information requested, e.g., a patient's chart, and the name of the patient. In response, the primary computer system may require some identification information, such as a login name and password for security purposes. Upon providing the identification information, the primary computer system transmits the requested information to the patient room computer system, completing load operation 802. At this time, the healthcare professional has access to the requested patient's chart. Although flow 800 relates primarily with the loading of a single patient record onto a patient room computer system, in practice many different patient records may be loaded onto the computer system during a session and later recalled individually when needed. More details on automatic and semi-automatic loading and/or downloading of patient information 802 information are discussed below in conjunction FIG. 9.

Next, edit operation 804 edits the patient's chart. During a typical scenario, the healthcare professional edits the chart during the patient's visit. Although this step may occur following the visit, such late entry reduces the ability to improve the efficiency of the visit, as information will not be shared with other computer systems during the visit. Therefore, it is contemplated that this information will most likely be entered during the visit.

In the embodiment shown in FIG. 8, upon entry of information into the patient's chart, transmit operation 806 transmits the update information to the primary computer system. Upon receiving the information, store operation 808 stores the updates on the primary computer system. In other embodiments, upon receiving and storing transmitted information, another step of displaying the updated information on the primary computer system may be implemented. Displaying the information allows for a nurse or other individual to monitor the updates to the chart and provide improved service to the patient by anticipating different needs such a medicine needs, medical supply needs, and/or billing needs. More details on the simultaneous display/monitoring of the updated information can be found in U.S. patent application Ser. No 10/610,777, entitled SYSTEM AND METHOD FOR MONITORING PATIENT HEALTHCARE INFORMATION DURING A VISIT, previously incorporated by reference.

Figure 9:
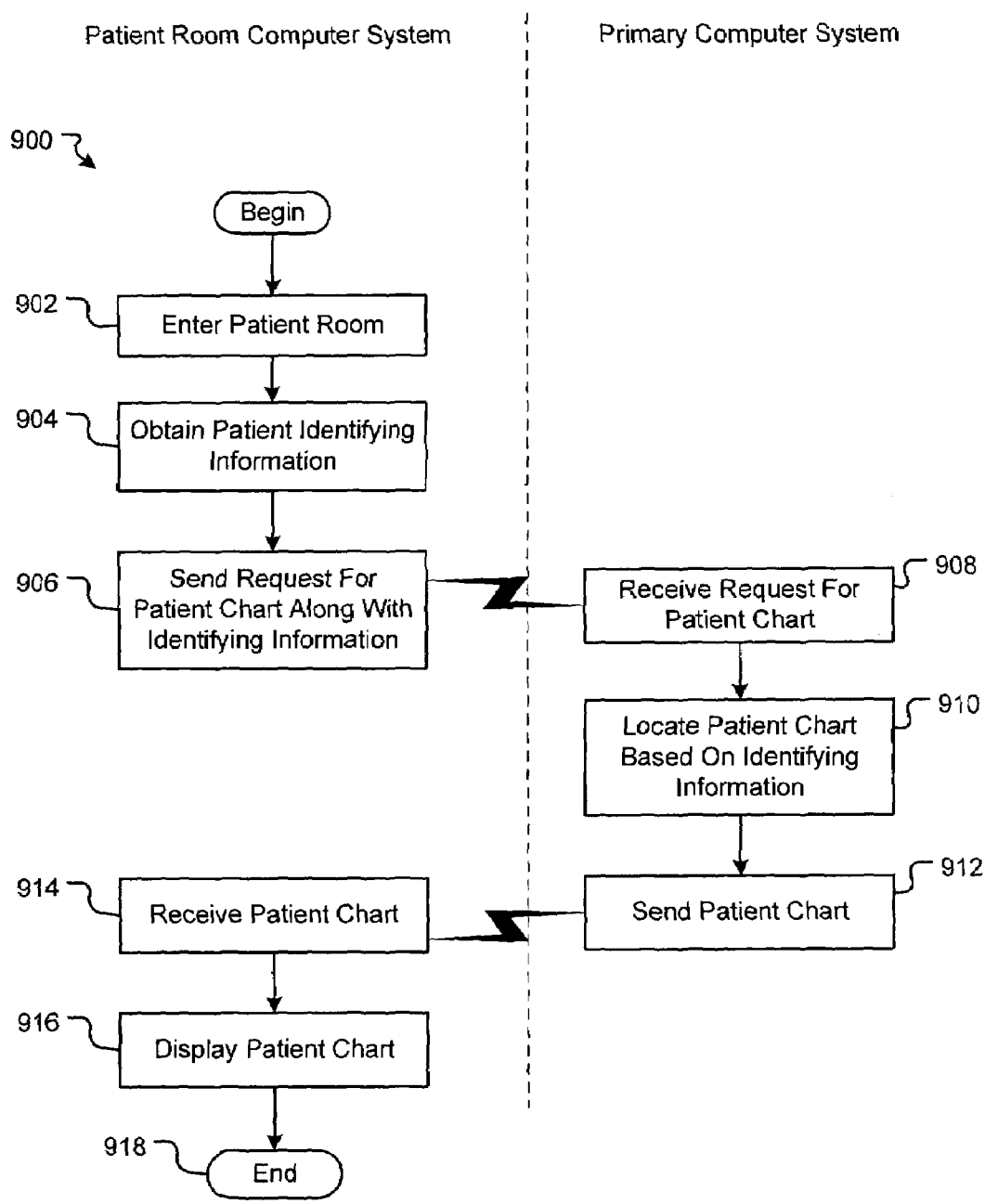
FIG. 9 illustrates a flowchart of functional operations related to loading an electronic version of a patient chart onto a patient room computer system in accordance with an embodiment of the present invention.

FIG. 9 illustrates a flowchart of functional operations related to loading and displaying of a patient chart on a patient room computer system, such as system 102 shown in FIG. 1, in accordance with an embodiment of the present invention. Prior to flow 900, it is presumed that an electronic version of a patient chart has been created and stored on a computer system, such as primary computer system 104 shown in FIG. 1. Alternatively, the electronic version of the patient chart may be stored elsewhere, yet the primary computer system has access to that patient chart. Also, the patient chart may be recalled using proper identifying information, such as the patient's name, social security number, or in some cases, the room number associated with the room the patient is located.

Initially flow 900 begins with enter operation 902 wherein the healthcare professional desiring the patient chart enters the patient room. The patient room in this scenario is the room in which the patient is receiving treatment or is otherwise located. In general, the enter operation 902 may also relate to the patient room computer system being carried into the patient room as well. Indeed, it is contemplated that the healthcare professional carries a patient room computer system from room to room.

Next, obtain operation 904 obtains the patient identifying information. Obtain operation 904 relates to the entering of patient information wherein the patient information relates to either patient-dependent data or patient-independent data. The term, "patient-dependent data," as used herein relates to data that is unique to the patient and is relatively permanent such that no other patient shares this information, e.g., the patient's name, social security number, address, telephone number or some combination of the above. The term, "patient-independent data" relates to other identifying features that may be unique to the patient for a short period of time, such as the patient's room number while the patient is in the hospital or doctor's office, a bar-code value, etc. Obtaining this identifying information allows the patient room computer system, such as 102 shown in FIG. 1, to request the proper patient chart from the primary computer system, such as 104 (FIG. 1).

Obtain operation 904 may occur in many different ways. In one embodiment, the user of the patient room computer system simply enters the room or patient identifying information into the patient room computer system. In another embodiment, a bar code is associated with a room and/or a patient. Using a bar-code reader communicably attached to the patient room computer system, the bar code may be read and thus obtain the patient identifying information. In yet another embodiment, the patient room computer system may receive a signal from a transmitter located in the patient room. The received signal, in this case, includes room (and therefore patient) identifying information.

Upon obtaining the patient identifying information, send operation 906 sends a request for the patient chart. Send operation 906 relates to the patient room computer system communicating with the primary computer system. Additionally, the request includes patient identifying information to enable the primary computer system to retrieve the proper patient chart. Following send operation 906, receive operation 908 receives the request. Receive operation 908 relates to the primary computer system receiving the request from the patient room computer system. Many known protocols and communication platforms may be used to implement this send/receive communication.

Upon receiving the patient chart request, locate operation 910 locates the patient chart based on the identifying information. Locate operation relates to a computerized method of searching stored records in a patient chart database, such as database 606 shown in FIG. 6. Using the identifying information, locate operation is able to uniquely identify, and retrieve the proper patient chart. Once located, send operation 912 sends the chart to the patient room computer system, which in turn receives the chart at receive operation 914.

Next, display operation 916 displays the patient chart. Displaying the patient chart may involve the display of information as shown and described above in conjunction with FIGS. 4 and 5. Additionally, flow 900 may further include a level of security (not shown) that requires the user to enter a user name and password before either sending a request for a patient chart 906 or displaying a received patient chart 916, or both. Depending on the security level, the authorization process may be located either on the patient room computer system or on the primary computer system, or both.

Following display operation, the flow 900 ends at end operation 918. Although not shown in FIG. 9, it is contemplated that once the chart is displayed, the healthcare professional is able to manipulate or otherwise edit the chart. Upon editing, the updates are transmitted back to the primary computer system to be stored and therefore managed.

Using the above methods and system, patient medical information, and in particular, patient charts can be safely stored and backed up since such documents are kept electronically. Also, the charts can be displayed or otherwise provided to a healthcare professional relatively quickly, i.e., automatically or semi-automatically without requiring the manual steps of searching for a paper chart, pulling the paper chart and handing the paper chart to the healthcare professional. Also, since paper charts are not handed back and forth, the chances of inadvertently transmitting diseases are reduced. Moreover, given that the electronic patient charts of the present invention are supplied based on requests using patient identifying information, whether patient-dependent or patient-independent, the chances of retrieving the wrong patient chart are greatly reduced.

It will be clear that the present invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed and as defined in the appended claims.

What is claimed is:

1. A method, comprising:
   using a patient room computer system, obtaining patient identifying information corresponding to room identification information for a patient;
   requesting an electronic patient chart from a primary computer system based on the room identification information;
   automatically, upon entry into a patient's room, receiving the electronic patient chart from the primary computer system based on the patient identifying information obtained;
   automatically, upon entry into the patient's room, displaying the patient chart on the patient room computer system based upon the patient identifying information obtained;
   when supplemental patient chart data is available, modifying the patient chart with the supplemental patient chart data; and
   when supplanted patient chart data is available, modifying the patient chart with the supplanted patient chart data.

2. The method as defined in claim 1 wherein requesting and receiving the patient chart use an intranet.

3. The method as defined in claim 1 wherein requesting and receiving the patient chart use the Internet.

4. The method as defined in claim 1 wherein requesting and receiving the patient chart use a wireless connection.

5. The method as defined in claim 1 wherein the room identification information is automatically transmitted to the patient room computer system upon entering the room.

6. The method as defined in claim 1 wherein obtaining the patient information comprises:
   reading a bar code to determine a bar-code value; and
   requesting the patient information associated with the bar-code value.

7. The method as defined in claim 6 wherein the bar-code provides the room identification information.

8. The method as defined in claim 7 wherein the bar-code provides patient identification information independent of the room identification information.

9. The method as defined in claim 1 wherein requesting a patient chart occurs automatically following receipt of patient identifying information; and wherein displaying the patient chart occurs automatically following receipt of the patient chart.

10. A storage medium on which is encoded instructions for performing a method of loading an electronic patient chart on a patient room computer system the method comprising:
   using the patient room computer system to obtain patient identifying information corresponding to room identification information for a patient;
   requesting the electronic patient chart from a primary computer system based on the room identification information;
   automatically receiving, upon entry into a patient's room, the electronic patient chart from the primary computer system based on the patient identifying information obtained;
   automatically displaying, upon entry into the patient's room, the patient chart on the patient room computer system based on the patient identifying information, obtained;
   when supplemental patient chart data is available, modifying the patient chart with the supplemental patient chart data; and
   when supplanted patient chart data is available, modifying the patient chart with the supplanted patient chart data.

11. A system, comprising:
   means for using a patient room computer system to obtain patient identifying information corresponding to room identification information for a patient;
   means for requesting an electronic patient chart from a primary computer system based on the room identification information;
   means for automatically receiving, upon entry into a patient's room, the electronic patient chart from the primary computer system based on the patient identifying information obtained;
   means for automatically displaying, upon entry into a patient's room, the patient chart on the patient room computer system based upon the patient identifying information obtained;
   when supplemental patient chart data is available, then means for modifying the patient chart with the supplemental patient chart data; and
   when supplanted patient chart data is available, then means for modifying the patient chart with the supplanted patient chart data.

12. The system according to claim 11, further comprising means for receiving the patient chart using an intranet.

13. The system according to claim 11, further comprising means for receiving the patient chart using the Internet.

14. The system according to claim 11, further comprising means for receiving the patient chart using a wireless connection.

15. The system according to claim 11, further comprising means for automatically transmitting the electronic patient chart to the patient room computer system upon entry into the room.

16. The system according to claim 11, further comprising means for reading a bar code to determine a bar code value, and means for requesting the patient information associated with the bar code value.

17. The system according to claim 16, further comprising means for providing the bar code as the room identification information.

* * * * *